United States Patent [19]

Baranczuk et al.

[11] Patent Number: 4,855,125
[45] Date of Patent: Aug. 8, 1989

[54] IODINATED ESTRADIOLS, INTERMEDIATE PRODUCTS AND METHODS OF PRODUCTION

[75] Inventors: Richard J. Baranczuk, Overland Park; Jay Spicer, Kansas City; William P. Duncan, Prairie Village, all of Kans.; Gary A. Rotert, Kansas City, Mo.

[73] Assignee: Bio-Medical Research Laboratories, Overland Park, Kans.

[21] Appl. No.: 102,315

[22] Filed: Sep. 25, 1987

Related U.S. Application Data

[63] Continuation of Ser. No. 663,571, Oct. 22, 1984, abandoned.

[51] Int. Cl.$^4$ ............ A61K 43/00; A61K 31/56; C07J 1/00
[52] U.S. Cl. .................... 424/1.1; 260/397.5; 514/182
[58] Field of Search ............ 424/1.1; 514/182; 260/397.5

[56] References Cited

U.S. PATENT DOCUMENTS

| | | |
|---|---|---|
| 2,855,413 | 10/1958 | Mueller . |
| 3,784,576 | 1/1974 | Counsell . |
| 3,859,429 | 1/1975 | Elias . |
| 3,959,455 | 5/1976 | Ansari et al. . |
| 4,041,145 | 8/1977 | van der Week . |
| 4,048,297 | 9/1977 | Counsell et al. . |
| 4,062,733 | 12/1977 | Edwards et al. . |
| 4,279,887 | 7/1981 | Baldwin et al. . |
| 4,290,965 | 9/1981 | Stocklin et al. . |
| 4,298,591 | 7/1981 | O'Brien, Jr. et al. . |
| 4,331,647 | 5/1982 | Goldenberg . |
| 4,465,676 | 8/1984 | Hochberg . |

OTHER PUBLICATIONS

Huffman, Max N. and Lott, Mary Harriett, "16-Substituted Steroids IV, 16-Keto-Alpha-Estradiol and 16-Ketoestrone"; J. Biol Chem., (1948), 172, 325.
Leeds, Norma S., Fukushima, David K. and Gallagher, T. F., "Studies of Steroid Ring D Epoxides of Enol Acetates"; A New Synthesis of Estriol and of Androstane-3-beta, 16-Alpha, 17-beta-triol; J.A.C.S., 76, 2943, (1954).
Soloway, A. H., Considine, W. J., Fukushima, David K. and Gallagher, T. F.; "Some Reactions of Epoxides of Steroid Enol Acetates"; J.A.C.S., 76, 2941, (1954).
Fishman, Jack and Biggerstaff, Warren R.; "Synthesis of 1,3,5(10)-Estratriene-3,16-beta, 17-Alpha-Triol"; J. Org. Chem. 23, 1190, (1958).
Mueller, G. P. and Johns, W. F.; "16-Alpha CHLORO and 16-Alpha-IODO Estrone Methyl Ether, New and Potent Lipid-Shifting Agents"; J. Am. Chem. Soc. 80, 1769, (1958).
Fajkos J.; "Steroids, Part XLIII, Comparison of the 16-Bromo-17-Ketones and 16-Bromo-17-Alcohols in the 3-Unsubstituted and 3-Beta-Oxygenated 5-Alpha-Androstane Series"; J. Chem. Soc. 3966, (1959).
Fieser, Louis F. and Feiser, Mary; STEROIDS Reinhold Publishing Corp., N.Y., (1967), p. 478.
Fishman, Jack; "Rearrangement of Steroidol Ring D Ketols", J.A.C.S., 82, 6143, (1960).
Mueller, George P. and Johns, Wm. F.; "The C-16 Halides of Estrone Methyl Ester"; J. Org. Chem., 26, 2403, (1961).
Fishman, Jack; "The Synthesis and Nuclear Magnetic Resonance Spectra of Epimeric 16-Deuterio-17-Beta- -and -17-Alpha-Estradiols", JACS, 87, 3455, (1965).
Hansen, Robert L.; "Perfluoroalkanesulfonate Esters as Alkylating Agents"; J. Org. Chem. 30, 4322, (1965).
Su, Tah Mun, Sliwinski, Wallace F., Schleyer, Paul von R., "The Solvolysis of Highly Unreactive Substrates Using the Trifluoromethanesulfonate (Triflate) Leaving Groups"; J.A.C.S. 91, 5386, (1969).
Anderson, Wayne K. and Veysoglu, Tarik; "A Simple Procedure for the Epoxidation of Acid-Sensitive Olefinic Compounds with M-Chloroperbenzoic Acid in an Alkyline Biphasic Solvent Systems", J. Org. Chem. 38, No. 12, 2267, (1973).
Baranczeck, Richard J.; "What's The Catch? Estrogen-Receptor Interaction"; Diagnostic Medicine, 1978.
Baranczeik, Richard J., "A New Tool in the Fight to Control Advanced Breast Cancer"; Diagnostic Medicine, 1978.
Hochberg, Richard B.; "Iodine-125-Labeled Estradiol: A Gamma-Emitting Analog of Estradiol that Binds to the Estrogen Receptor"; SCIENCE, 205, 1138, (1979).
Hochberg, R. B. & Rosner, W.; "Interaction of 16-Alpha-[$^{125}$I]Iodo-Estradiol with Estrogen Receptor and Other Steroid-Binding proteins"; Proc. Nat'l. Acad. Sci. U.S.A., 77, No. 1, 328, (1980).
Heiman, Daniel F., Senderoff, S. G., Katzenellenbogen, J. A. & Neeley, R. J.; "Estrogen Receptor Based Imaging Agents, 1. Synthesis and Receptor Binding Affinity of Some Aromatic and D-Ring Halogented Estrogens"; J. Med. Chem., 23, 994, (1980).
Longcope, C., Arunachalam, T. Rafkind I. & Caspi, E.;

(List continued on next page.)

Primary Examiner—Leonard Schenkman
Assistant Examiner—Joseph A. Lipovsky
Attorney, Agent, or Firm—Litman McMahon & Brown

[57] ABSTRACT

A method of preparation of estradiol derivatives labeled by iodine, especially $^{123}$I, substitution at C-16 are synthesized according to the present invention. A triflate intermediate is prepared from which either 16-alpha-$^{123}$I-17-beta-estradiol or 16-beta-$^{123}$I-17-beta-estradiol are prepared by described methods. Both 16-alpha-$^{123}$I- and 16-beta-$^{123}$I-17-beta-estradiol made according to the methods described herein have a high relative specific acitvity. The methods are sufficiently rapid so that the relatively short half-life of $^{123}$I is readily accommodated without substantial radioactive decay of the label.

8 Claims, No Drawings

OTHER PUBLICATIONS

"Biological Activity of [$^{127}$I] and [$^{125}$I] Estradiol Analogs in Vitro and In Vivo"; Journal of Steroid Biochemistry, 14, 261, (1981).

Katzenellenbogen, J. A.; Senderoff, S. G., Carlson, K. E., McElvaney, K. D. & Welch, M. J., "Gamma-Emitting Estrogens: Development of Imaging Agents for Breast Tumors (Meeting Abstract)"; Journal of Steroid Biochemistry, (1981), It is Belived that the Article is that Referred to as Reference 24 Below.

Katzenellenbogen, J. A.; "The Development of Gamma-Emitting Hormone Analogs as Imaging Agents for Receptor-Positive Tumors", The Prostatic Cell: Structure and Function, Part B, 313-327, (1981), Applicants believe they received the reference directly from the author & they have been unable to locate a literature, cite for the reference.

Argentine, M. Zahner, M. & Schubiger, F. A.; "Comparison of Several Methods for the Synthesis of W-Iodine-123-Hepta-decanoics Acid", Journal of Radioanalytical Chemistry, 65, No. 1-2, 131, (1981).

McElvaney, K. D., Carlson, K. E., Welch, M. J., Senderoff, S. G., Katzenellenbogen, J. A. & the Los Alamos Medical Radioisotope Group; "In Vivo Comparison of 16-Alpha-[$^{77}$BR] Bromoestradiol-17-Beta and 16-Alpha-[$^{125}$I] Iodoestrodiol-17-Beta", Journal of Nuclear Medicine, 23, 420, (1982).

McEbvaney, K. D., Katzenellenbogen, J. A., Shafer, K. E., Siegel, H. A., Senderoff, S. G., Welch, M. J. and the Los Alamos Medical Radioisotope Group; "16-Alpha[$^{77}$BR] Bromoetradiol: Dosimetry and Prelimanary Clinical Studies", Journal of Nuclear Medicine, 23, 425, (1982).

Oxley, D. K., Haven, G. T. Wittliff, J. L. & Gilbo, D.; "Precision in Estrogen & Progesterone Receptor Groups, Results of the First CAP Pilot Survey"; A.J.C.P., 78, 587, (1982).

Duffy, M. J.; "Short Communication, Array of Estradiol Receptors in Human Breast Carcinomas Using the Gamma Emitting-Ligand 16-Alpha[$^{125}$I] Iodoestradiol"; Journal of Steroid Biochemistry, 16, 343, (1982).

Therain, F., Gros, J. & Souchu, A., "Synthesis du $^{123}$I--16 Iodo Estradiol", Journal de Biophysiquice et de Medicines Nucleaire, 6, 155, (1982), translation attached.

Landvatter, S. W., Katzenellenbogen, J. A., McElvaney, K. D. and Welch M. J.; "Preparation and Properties of Halogenated Estrogens as Imaging Agents for Breast Tumors", Symposium Abstracts, Journal of Labelled Compounds and Radiopharmaceuticals, XIX, Nos. 11-12, 1293, (1982).

McElvaney, K. D., Carlson, K. E., Katzenellenbogen, J. A. & Welch, M. J., "Factors Affecting the Target Site Uptake Selectivity of Estrogen Radiopharmaceuticals; Serum Binding and Endogenous Estrogens", Journal of Steroid Biochemistry, 18, No. 6, p. 635, (1983).

"The Radiopharmaceutical Science Council Newsletter", Fall, 1984; pp. 13-14.

Chemical Abstracts; vol. 98, (1983), #215878B; Therain et al.

Fishman et al.; "Synthesis of 1,3,5(10)-estratriene-3,-16-$\beta$, 17$\alpha$Triol"; J. Org. Chem., 23, 1190, (1958).

Arunachlam et al., "Journ. Bio. Chem.", 254, No. 13, (1979), pp. 5900-5905, Note Especially p. 5904.

Beard Charles D. Baum, Kurt and Grakaushas, Vytautas; "Synthesis of Some Novel Trifluoromethanesulfates and their Reactions with Alcohols"; J. Org. Chem. 38, No. 21, 3673 (1973).

Howells R. D. and The Crown, J. D.; "Trifluoromethanesulfonic Acid and Derivatives"; Chemical Reviews, 77, No. 1, 69 (1977).

IODINATED ESTRADIOLS, INTERMEDIATE PRODUCTS AND METHODS OF PRODUCTION

CROSS-REFERENCE TO RELATED APPLICATIONS

The present application is a continuation of U.S. Ser. No. 663,571, filed Oct. 22, 1984, now abandoned.

BACKGROUND OF THE INVENTION

Certain research related to the subject matter of the present application was conducted under monetary grants from the United States of America and a paid up, nonexclusive, irrevocable and non-transferable license is hereby granted to the United States of America for governmental purposes.

This invention relates to estradiol derivatives, their syntheses and the preparation of their synthetic intermediates or precursors. In particular, this invention relates to the preparation of certain substituted estradiols which have a specific, preferred sterochemistry.

The term "estradiol", as used herein, refers to compounds having the following general structural formula:

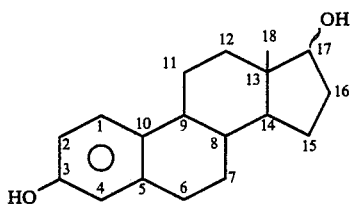

Estradiols similar to the compound I are, generically, estra-1,3,5-(10)-triene-3,17-diols. In the above drawing the carbons in the estradiol structure are numbered according to the generally recognized nomenclature system for steroids, with the hydroxy substituents located at the 3- and 17-positions. It will be understood that the substituent at the 17 position may have either of two orientations, referred to as alpha and beta. Generally, an alpha substituent is one which projects beneath the plane of the drawing shown above and a beta substituent is one which projects above the plane of the steroidal ring drawing. The same would be true for substituents located at C-16.

Substance II shown below is a form of estradiol generally medically recognized to be of particular importance and has a 17-hydroxy-substituent located beta. A commonly used name for this substance is estra-1,3,5(10)-triene-3,17-beta-diol (17-beta-estradiol or beta-estradiol).

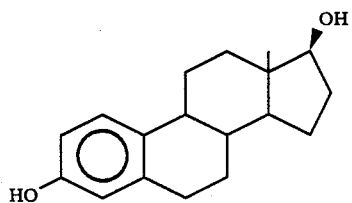

In general, many estradiols are naturally occuring substances whose derivatives have been found to have medicinal use. For example, the 3-methyl ether has been used for replacement therapy in estrogen deficiency. Also, certain radioactively labeled estradiols may be used in estrogen receptor assays. In particular, the tritiated, iodine-125(I-125) and bromine-77(Br-77) labeled substances have been tested.

It is known that estrogen receptors, i.e. binding substrates for estradiols, may be found in certain animal tissues. It has also been found that the presence of estrogen receptors may be connected with certain abnormalities in the tissue. Estradiols, if properly labeled, may be utilized to detect the presence of these estrogen receptors in tissue. The medical profession generally theorizes that these estrogen receptor analyses may be conducted in vitro or in vivo. Further, applicants foresee that appropriately labeled estradiols may be utilized to deliver a radioactive iodine, especially $^{123}$I, to a site in tissue, in order to promote a therapeutic effect.

In particular, certain 17-beta-estradiols, which have been substituted at the 16-position, are generally thought to have an affinity for estrogen receptors which is both significant and useful in performing estrogen receptor analyses, including assays and imaging. It is foreseen that numerous 16-substituted-17-beta-estradiols may be of importance, particularly those in which the 16-substituent is a halogen and most importantly when the halogen is radioactive iodine, especially $^{123}$I, which has a relatively quick half life and high energy radiation associated with decay thereof. It is foreseen that both 16-alpha-16-beta-substituted-estradiols may be of use. However, for any given substituent, the affinity of the 16-alpha-substituted-17-beta-estradiol, for estrogen receptors, is likely to differ from that for the analogous 16-beta-substituted-17-beta-estradiol.

Since both the 16-alpha-substituted and 16-beta-substituted-17-beta-estradiols are foreseen to have utility, it is prefered that methods of syntheses of each be developed. It is preferable that each synthetic scheme yield a desired isomer substantially stereospecifically, so that problems of purification and problems from the differences of affinity of the two isomers for binding sites, are avoided. Thus, two general synthetic schemes are needed, one which provides 16-alpha-substituted compound with very little 16-beta-substituted compound being present, and a second general reaction methodology which yields 16-beta-substituted compound with very little 16-alpha-substituted compound being present.

It is readily seen that it would be most desirable to develop a single synthetic precursor or intermediate from which either the 16-alpha- or the 16-beta-substituted compound can be relatively very rapidly and easily formed. That is, given a supply of the synthetic intermediate a synthesis laboratory could easily prepare whichever 16substituted compound is desired. It is particularly desirable to have alternate synthetic schemes which are relatively easy to conduct and which are both very rapid and very efficient and which produce a relatively high percentage of the desired final product.

With present technology, two basic methods of detection of labeled estradiols are most available. In one, a radioactive substituent is introduced into the molecule and standard methods of radioisotope detection are utilized to determine the presence of the labeled estradiol in the animal tissue, either in vitro or in vivo. In the other, nuclear magnetic resonance (NMR) methods are utilized to detect certain nucleii, and generally non-radioactive labels may be used. At the present time, only radioisotope techniques are widely available but it is foreseen that other methods may be come more available in the future.

If a radioactive isotope is used as the label, then the stereospecificity of the reactions leading to the synthesis of the 16-substituted-17-beta-estradiol may be critical. Also, efficiency of the reaction, in terms of product yield and the length of time it takes to introduce the radioactive isotope into the molecule and then isolate the desired product for diagnostic or therapeutic use, may be very important.

The importance of the stereospecificity is easily understood. Radioactive labels are very expensive and if the reaction is not sufficiently stereospecific large amounts of the label may be lost in undesired products. Also, if the undesired products are to be discarded there may be problems with dangerous residual waste-product radioactivity. Finally, side products might not be easily separable from the desired isomer, and they can interfere with the certainty of assay and imaging data collected when the product is used in medicinal analyses.

If the product yields are not sufficiently high, much of the radioactive isotope may not be incorporated into a useful product, again wasting expensive isotope.

If the reactions involved in the introduction of the radioisotope into the molecule, when coupled with any further reactions or purifications necessary to isolate the desired radioactive products, are not sufficiently rapid, special problems may be encountered. It will be understood that the radioactive label is constantly decaying; and, if the isotope has a sufficiently short half-life, it must be introduced into the molecule rapidly, and the compound must be isolated for biological use relatively rapidly, or the isotope will have passed through sufficient half-lives to produce so little "hot" or radioactive substrate that detection may be difficult.

In some instances the radioisotope used may be contaminated with small amounts of other radioisotopes of the same compound. For example, Iodine-123 (I-123) as it is currently made, is often contaminated with some Iodine-124 (I-124). The half-life for I-123 is about 13.3 hours whereas the half-life for I-124 is about 4.2 days. I-123 is readily detectable and gives clear images whereas I-124 generally causes some scattering and images of low resolution. Consider what happens if a mixture of 99 to 1 I-123 to I-124, is utilized to label a substrate. If the reaction takes too long, for example 26 hours, for introduction of the isotope into the substrate molecule and isolation of the desired product, then the I-123 will pass through about two half-lives and only about 25% of it will be left. The I-124, however, will have barely begun decaying and nearly 100% of it will be left. The ratio of I-123 to I-124, after the 26 hours, will have changed to approximately 24 to 1. It is readily seen that this enhancement of the amount of I-124 present, by ratio, may cause difficulty since the I-124 might make resolution of images difficult. Also, if much of the isotope mixture must be given to accommodate imaging of I-123, residual radioactivity from the I-124 component, with its long halflife, may be a problem. These types of problem are usually present whenever an isotope of short half-life is used, if the isotope is normally contaminated by a second isotope of longer half-life.

In some instances, the decayed product may still be active as far as an estrogen receptor is concerned and the labeled, but no longer hot, estradiol derivative may block estrogen receptors from receiving the hot substrate, thus interfering with the accuracy of any assay or imaging data obtained. This problem cannot be overcome by using an excess of the estradiol material since doing so may tend to overload the estrogen receptors and send hot estradiol to other locations, where it may be detected, generating erroneous conclusions about the presence of estrogen receptors.

When non-radioactive isotopes are used in chemical syntheses, problems of low yield and low specificity are often overcome by utilizing large amounts of starting materials, and labels, and undergoing sufficient purifications to allow for the isolation of significant amounts of the desired products. It is clear that this methodology is generally unacceptable when radioactive labels are used. First, radioactive labels are usually too expensive for an inefficient synthesis scheme to be commercially utilizable. Secondly, radioactive isotopes can be dangerous and large concentrations of them should be avoided. Also, unreacted starting materials and undesired side products may be radioactive, causing problems with contamination during clean-up, isolation and waste material disposal. Further, if the isolation of the desired product takes too long there may be problems with decay of the isotope.

Radioactive isotopes of the halogens are generally considered to be the most important types of labels for use in labeling compounds for biological assays and imaging. The isotopes generally considered to be of most importance and suitable for labelling estradiol according to the present invention are fluorine-18 (F-18), bromine-77 (Br-77), iodine-123 (I-123) and iodine-125 (I-125).

Iodine-123 labelled estradiol is foreseen to be especially useful by applicants for all types of tissue imaging where the tissue has "estrogen" receptors. Iodione12 is a gamma emitter having a half-life of approximately 13.3 hours. Iodine-123's energy of gamma decay is relatively high, approximately 159 kilo-electron-volts (KeV). The toxicity of iodine is generally well understood, and I-123 is generally considered to be an almost ideal radioisotope for use in biological studies. In particular, its relatively short half-life makes radioactivity contamination a relatively minor problem, while at the same time, its relatively high energy of decay makes detection relatively easy, even in vivo.

In the past, 17-beta-estradiols labeled with I-123 at the 16-position have been unavailable in amounts and purities generally considered to be useful in assays, and other diagnostic work, either in vitro or in vivo, due to problems in their syntheses. Generally, these problems result from the length of time formerly required to introduce an I-123 label into the 16-position, stereospecifically, and the length of time required to complete the synthesis and isolate and purify the desired product. In addition, those synthetic methodologies which were considered in the past were often of low yield and often resulted in the waste of large amounts of I-123 label.

The advantages of the present invention, in preparing labeled compounds, will be most apparent if an examination is first made or previously known methods of introducing halo-substituents into the 16-position of 17-beta-estradiol. Such an examination, of the major known methods, follows:

A highly publicized method of preparing 16-alpha-halo-substituted-17-beta-estradiol is that published by R. B. Hochberg and will be generally referred to as Hochberg's method or synthesis. The final step of Hochberg's synthesis is shown below and comprises Iodo-substituents on the 16-beta-bromo-compound, i.e. a Finkelstein reaction:

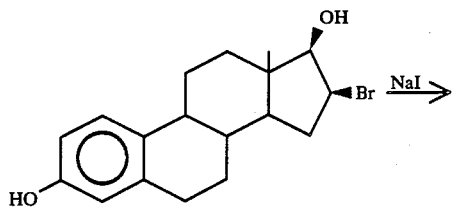

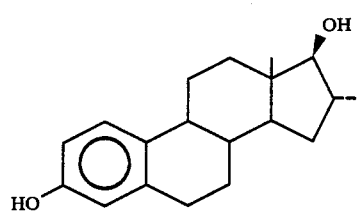

In the specification and claims of the present application: a wedge indicates a substituent projecting above the plane of the drawing; a dotted line indicates projection below; and, a curve indicates a mixture of both. These are conventional methods of indicating stereochemistry. Also, Ac is used to indicate an acetyl group, —C(O)CH₃.

The substitution reaction is generally run in 2-butanone for anywhere from 12 to 24 hours. Although the reaction has been utilized to introduce the radioisotope I-125 into the 16-alpha position of 17-beta-estradiol, it is generally considered to be of too low a yield and too long a length of time to allow efficient production of a compound by the substitution of a radioisotope, such as I-123, which has a relatively short half-life.

Even if conditions are found which allow for an increase in the rate of the substitution reaction, it appears unlikely that the synthesis and purification method proposed by Hochberg can be readily and economically utilized to prepare commercially useful 16-alpha-substituted radioactive estradiol derivatives when the radioactive isotope has a very short half-life. For example, the Hochberg synthesis may require time-consuming product isolations and purifications. Further, the reaction does not appear to be adaptable to substantially stereospecific preparation of 16-beta-substituted compound.

The following scheme shows the overall Hochberg method of synthesis:

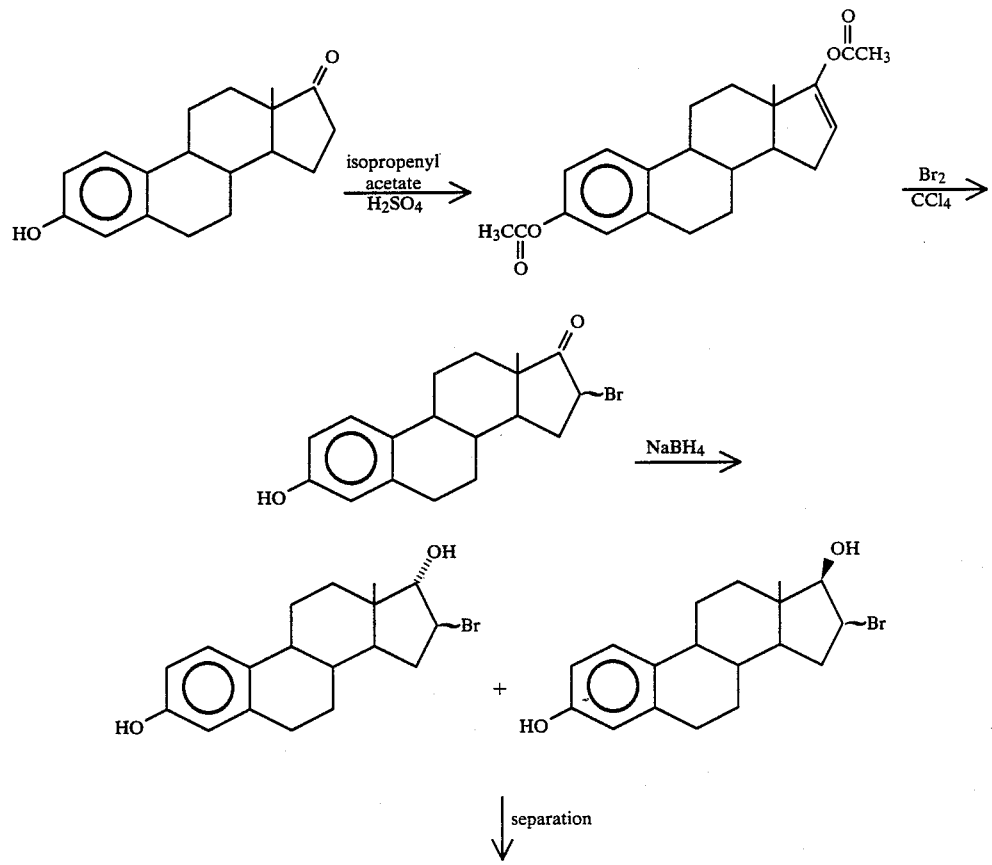

-continued

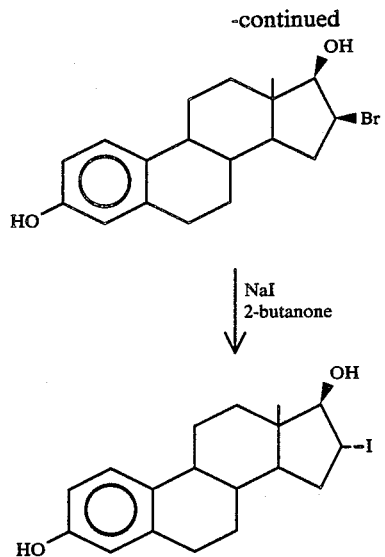

There are certain problems with the above reaction scheme. For example, the bromination step yields two compounds, mostly the beta form, and the reduction step gives a mixture of all four possible bromohydrins, from which the desired isomer has to be isolated. No single intermediate is formed from which the 16-alpha-substituted compound can be rapidly formed and from which the 16-beta-substituted compound can also be rapidly formed. Also, the starting material for the final Finkelstein, 16-beta-Br-17-beta-estradiol, and the product of the final substitution, 16-alpha-I-17-beta-estradiol, have similar characteristics for chromatographic purposes, so their clean separation from one another, in the event that the final substitution does not go to completion, can be difficult. Further, during the Finkelstein reaction and work-up there may be epimerization of starting material or product, thus decreasing efficiency. Also, one epimerization product, 16alpha-Br-17-beta-estradiol, has very similar chromatographic properties to the desired product, making purification somewhat difficult.

Accordingly, researchers' initial attempts to form 16alpha-[125]I-17-beta-estradiol via the Hochberg method resulted in products have specific activities which were very low, approximately 95 to 140 Curies per millimole (Ci/mole), as opposed to the theoretical specific activity of approximately 2,000 Ci/mmole. It is reported in the literature that meticulous purification of the 16-beta-Br-17-beta-estradiol used in the Finkelstein reaction has resulted in some increased specific activity; however, purity of products still appears to be a problem and seems to keep specific activity down.

Another, practical, problem is associated with Hochberg's method. Most radioactive halogen anions are commercially available in the form of an ammonium salt or a sodium salt. In the case of radioactive iodides both ammonium salts and sodium salts are usually available whereas, in the case of the bromides and fluorides, usually only the sodium salt is available. These radioisotopes are normally shipped in water, which does not readily evaporate, and significant amounts of base, either sodium hydroxide or ammonium hydroxide, will be present. The Finkelstein reaction, and its starting material, may be sensitive to the presence of either base or water. Therefore, the commercially available isotope, in its basic storage mixture, usually must be scrupulously neutralized and dried before it can be utilized. It is evident that it would be desirable to develop a reaction methodology which is at least relatively insensitive to the presence of water and preferably can tolerate base.

An alternative method of labeling 17-beta-estradiol with halogens at the 16-position has been developed and utilized by Katzenellenbogen et al. Their general reaction methodology is shown below:

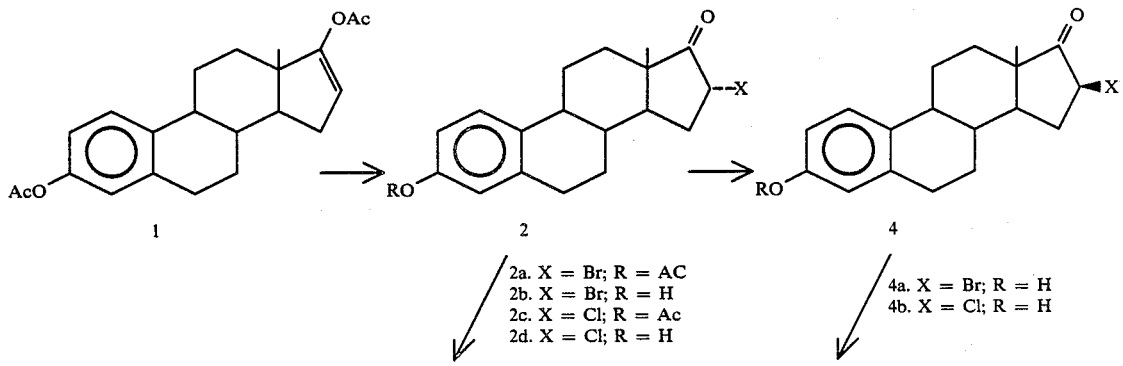

-continued

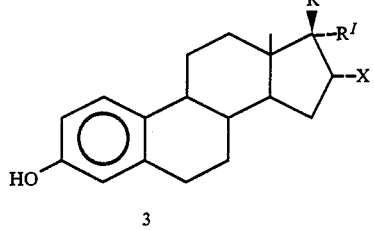

3

3a. X = Br; R = OH; R$^I$ = H
3b. X = Br; R = H; R$^I$ = OH
3c. X = Cl; R = OH; R$^I$ = H

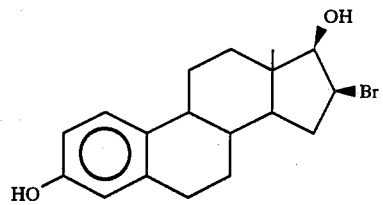

5

3d. X = Cl; R = H; R$^I$ = OH

Katzenellenbogen et al. J. Med. Chem., 23, p. 994–1002 (1980) describe bromination of the enol acetate (1) followed by hydrolysis to give 16-alpha-Br-3-hydroxy-1,3,5(10)-triene-17-one(16-alpha-Br-estrone; (2b) as proceding with relatively high yield and relatively high specificity for the alpha-product (2b). Formation of the 16-beta-Br-compound, 4a, was accomplished by epimerization of the 16-alpha-compound (2b) in acid. The epimeric ratio was 1/1.8 (2b/4a). In commercial use, such a mixture would have to be separated by chromatography and clean separation can be expected to be difficult and time-consuming.

16-alpha-Br-17-beta-estradiol (3a) was formed from reduction of the ketone (2a) with lithium aluminum hydride. (LiAlH$_4$). The reduction yields both the 17-alpha-and 17-beta-alcohols (3a and 3b) in a ratio of 2/1 (17-beta/17-alpha; 3a/3b). Such a mixture can, in theory, be separated by chromatography; however, again, since the products are so similar, chromatographic separation may be expected to be difficult and time-consuming.

Katzenellenbogen prepares Hochberg's precursor, compound 5 above, by reduction of a mixture of 16-alphaand 16-beta-Br-estrones with zinc borohydride (ZnBH$_4$). All four bromohydrins are formed from such a reduction, since the reduction is not stereospecific. Again, although chromatographic means may in theory be utilized to separate the four bromohydrins, they are similar enough in properties so that the separation can be expected to be very difficult.

16-alpha-Cl-estrone (2c) was formed by Katzenellenbogen et al., by treating the enol acetate (1) with tert-butyl hypochlorite. A mixture of products is generally formed from such a reaction so some purification is necessary for isolation of the chloride.

16-alpha-Cl-17-beta-estradiol (3c) and 16-alpha-Cl-17-alpha-estradiol (3d) are formed from treatment of the estrone (2c) with LiAlH$_4$. Isolation of either product requires purification generally by chromatography, which can be difficult with such similar reaction products.

It may be appreciated from the above that the variation of the Hochberg method utilized by Katzenellenbogen et al. is generally inefficient for 16-substituted compounds, especially when radioisotopes are being used. First, in nearly all instances, product mixtures are formed, which wastes expensive label and which can be hard to separate. Also, too much time may be needed to easily handle radioisotopes of relatively low half-lives.

Longcope et al. have developed a method of synthesis for 16-beta-I-17-beta-estradiol which is significantly different from Hochberg's synthesis and the Katzenellenbogen variations. Their synthesis begins with 16-alpha-17-beta-estriol and is shown below:

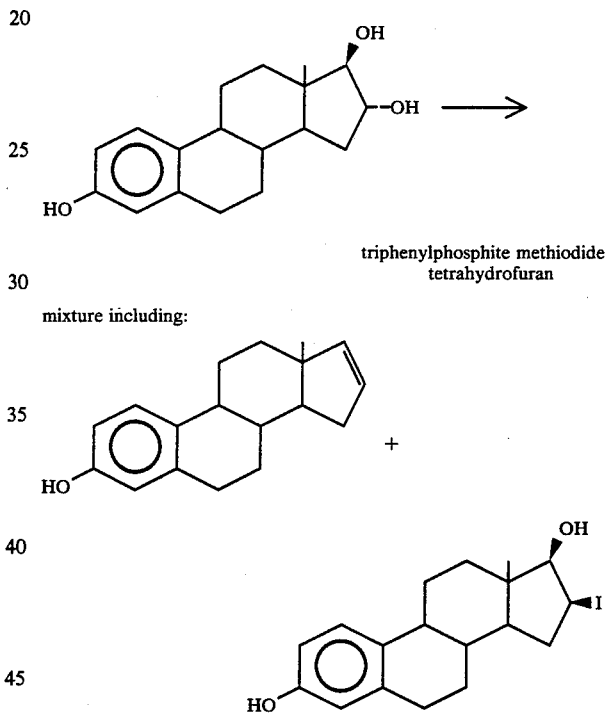

The Longcope method yields a product mixture which includes the desired beta-product together with an elimination product, so, again, it is inefficient. Secondly, it cannot be readily adapted for formation of 16-alpha products. Also, radioactive triphenylphosphite methiodide is expected to be difficult to prepare. In addition, it does not appear to be easily adaptable to the utilization of other halogens and their radioactive isotopes.

The above three general synthetic methodologies illustrate many of the problems associated with syntheses of 16-substituted, either alpha- or beta-, 17-betaestradiols. Generally, reaction mixtures including numerous products are formed. Also, no synthesis is readily adaptable to yield, stereospecifically, either the 16-alpha or the 16-beta isomer as desired. Also, the lengths of time required for the introduction of halogen label and isolation of the products tend to make the utilization of the above schemes for radioactive isotopes, especially isotopes with relatively short half-lives, very difficult, if not commercially impossible.

OBJECTS OF THE INVENTION

The principal objects of the present invention are: to provide a method of rapidly introducing a radioactive halogen, particularly $^{123}$I, into estradiol; to provide a general method of preparation of 16-halo-substituted-17-beta-estradiols; to provide such a method by which radioactive substituents, of relatively short half-lives, can be quickly and efficiently introduced into the 16-position of 17-beta-estradiols; to provide such a method by which substitution of the substituent into the 16-position of 17-beta-estradiols can be made either alpha or beta as desired, either substitution being made with nearly complete stereospecificity; to provide a synthetic intermediate for use in such a method of synthesis from which either 16-alpha-substituted-,or, 16-betasubstituted17-beta-estradiols can be relatively quickly, stereospecifically and efficiently derived; to provide a method by which 16-alpha-$^{123}$I-17-beta-estradiol, having a relatively high specific activity, suitable for use in estrogen receptor assays and imaging studies can be quickly, efficiently, and easily manufactured; to provide a method of synthesis by which 16-beta-$^{123}$I-17-beta-estradiol, having a relatively high specific activity and being suitable for use in estrogen receptor assays and imaging studies can be relatively quickly, stereospecifically and efficiently manufactured; to provide the products of such synthesis; to provide the specific product 16-alpha-$^{123}$I-17-beta-estradiol having a specific activity of greater than 2000 and preferably at least 5,000 Ci/mmole and being collected in sufficient amounts for utilization in estrogen receptor assays and imaging studies; to provide the specific product 16-beta-$^{123}$I-17-beta-estradiol; and to provide such methods of syntheses which are relatively easy to utilize, are economical and which are particularly well suited for their proposed usages.

Other objects and advantages of the present invention will become apparent from the following descriptions, wherein are set forth by way of illustration and example certain embodiments of the present invention. As required, detailed embodiments and examples of the present invention are disclosed herein. However, it is to be understood that the disclosed embodiments and examples are merely exemplary of the invention, which may be embodied in various forms. Therefore, specific details disclosed herein are not to be interpreted as limiting but rather merely as a basis of the claims and a representative basis for teaching those skilled in the art to variously employ the present invention.

SUMMARY OF THE INVENTION

It will be understood that certain superscripts used herein are also used in the claims. The superscripts are generally used consistently between the specification and claims. Therefor, the superscripts may not appear in numerical order in the claims or the specification.

The present invention is directed to a new synthetic method for preparing 16-halogen-substituted-17-beta-estradiols. In particular, a synthetic scheme is presented which permits the introduction of Iodine-123 (I-123) into either the 16-alpha- or 16-beta-position of 17-beta-estradiol, essentially stereospecifically, as desired. The nature of the synthesis is such that the desired product can be isolated, in relatively large and useful amounts, before the I-123 label, which has a relatively short half-life of approximately 13.3 hours, has decayed to such a point that the product mixture is no longer hot enough to be desirable for use in biological assays. Generally, I-123 can be introduced into 17-beta-estradiol in approximately one to two hours utilizing methods described herein such that the decay half-life of 13.3 hours is readily accommodated and excessive decay does not occur before the product can be beneficially utilized.

Also, it is foreseen that the general synthetic scheme developed is readily adaptable to the syntheses of other 16-substituted-17-beta-estradiol products. For example, it is anticipated tha 16-substituted fluorine, chlorine and bromine derivatives can be relatively quickly formed. Accordingly, it is foreseen that radioisotopes of the various halogens can be rapidly introduced into the 16-position of 17-beta-estradiols.

The synthetic scheme developed is readily adaptable for the highly stereospecific synthesis of either 16-alpha-halo-substituted-17-beta-estradiols or 16-beta-halo-substituted-17-beta-estradiols. In particular, a product solution including substantially only 16-alpha-halo-substituted-17-beta-estradiol can be obtained. Also, a product solution including substantially only 16-beta-halo-substituted-17-beta-estradiol can be obtained via a step modification in the reaction scheme. The term "stereospecific", as used herein, means that the product mixture includes substantially only the desired stereoisomer, be it 16-alpha or 16-beta.

The following reaction scheme outlines a general synthesis of either 16-alpha-halo-substituted or 16-beta-halo-substituted-17-beta-estradiols according to the present invention:

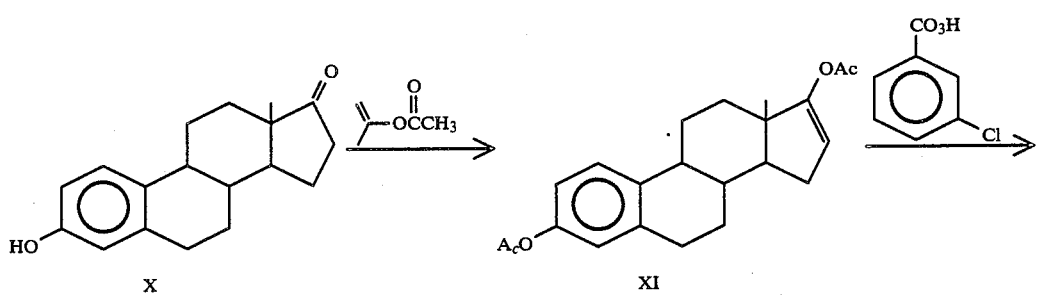

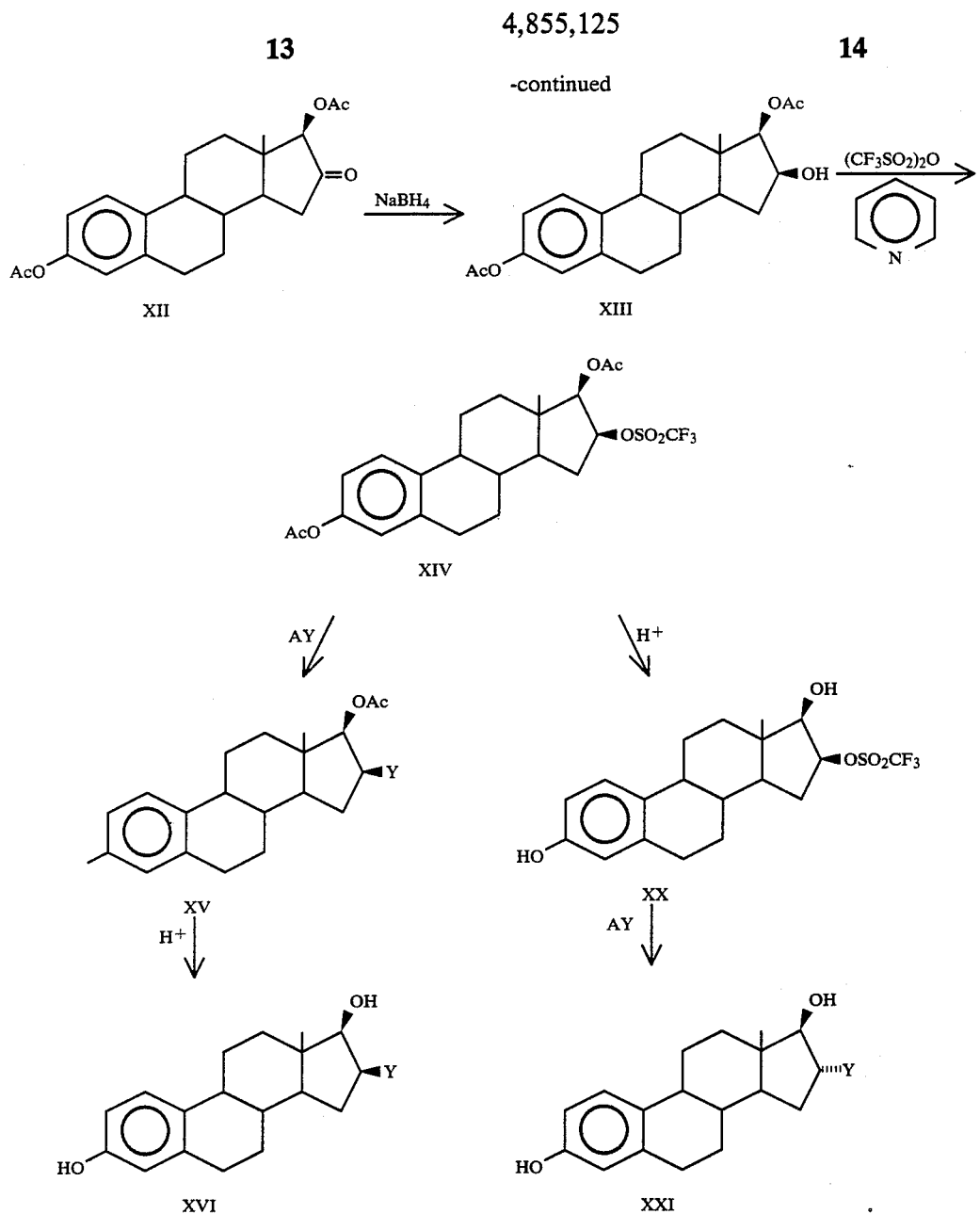

-continued

WHEREIN:
Ac is C(O)CH₃
AY is a slat of a halide with:
Y being halide ion; and A being cation For ease of reference the intermediates and products in the reaction scheme will be referred to, as indicated above, beginning with Roman Numeral X.

An important step in the synthesis involves the utilization of a synthetic intermediate XIV, a 16-beta-triflate-estradiol in which both the 3- and 17-beta-hydroxy groups have been protected with an acetate group. This intermediate is relatively stable and can be easily purified by high pressure liquid chromatography (HPLC). Also, it is relatively easily characterized and is relatively stable to the presence of water.

As shown in the reaction scheme, according to one series of reactions, the triflate diacetate XIV is hydrolized in acid to yield at 16-beta-triflate of 17-beta-estradiol, XX. Following this, the diol XX is treated with a nucleophile source, AY, to yield a product XXI in which the halogen substituent, Y, is located alpha on the 16-position. This latter substitution reaction occurs relatively rapidly, as will be seen from the examples below, and in generally high enough yield to make the synthesis commercially utilizable. Also, the substitution, which is believed to proceed via an $S_N2$-type mechanism, is generally observed to be relatively stereospecific.

Also as seen in the above reaction scheme, a 16-beta-halo-substituted-17-beta-estradiol derivative XVI can also be readily prepared from the same triflate intermediate XIV. According to the method of the invention, if the triflate diacetate XIV is reacted with a halide anion source AY, before hydrolysis to an estradiol, a 16-beta-halo-substituted-17-beta-estradiol, 3,17-beta-diacetate (XV) is formed. While the mechanism for this substitution is not fully understood, the reaction appears to be highly stereospecific and yields almost exclusively the 16-beta-halo-substituted product (XV). Presumably the 17-beta protecting group interacts with the triflate group at the 16-beta position to cause the substitution to occur in the manner observed.

If the diacetate product, XV, is then hydrolized, 16-beta-halo-substituted-17-beta-estradiol, XVI is readily isolated.

Numerous features of the above mentioned substitutions and hydrolyses make the synthetic scheme of the present invention highly advantageous. First, the 16-substituted halo-compounds are readily separated from the 16-beta-triflates, regardless of whether dihydroxy or diacetal, so the products from the substitutions can be easily separated from the starting material. This is due to the large difference in chromatographic properties between triflates and halogen compounds.

Secondly, the substitution reactions are relatively rapid so anions of isotopes which have relatively short half-lives can be utilized as the nucleophiles displacing the triflate group. In part, this is probably due to the nature of the triflate anion as a very good leaving group for substitution reactions.

Also, as mentioned above, the triflate group and the halo-substitution reactions thereon have been found to be relatively stable to the presence of water in the reaction mixture. It was also noted above that radioisotopes are normally only commercially available in aqueous suspension. Thus, the insensitivity of the triflate to water means that scrupulous drying of the isotope reagent is not necessary. However, some drying is preferred and normally is conducted.

The substitutions of the triflate group preferably utilize appropriate crown ether with the nucleophile.

The general source of radioactive halide ions is the sodium halide or the ammonium halide slat. It has been found that a useful crown either for complexing with the sodium and ammonium cations is 18-Crown-6. In the syntheses of the radio-labeled estradiols discussed herein, the crown ether is normally utilized in excess, since a very small amount of the halide is present in the reaction mixture. The excess of crown ether has not been found to cause any complications in the syntheses.

Another advantage to the present scheme is that for the halo-substitution of the triflate anion, the conditions are such that epimerizations of the products are kept to a minimum. Generally, the triflate anion is a very poor nucleophile and the conditions are such that epimerization is unlikely. By "poor nucleophile", it is meant that relative to the halogens, the poor nucleophile is unlikely to attack substrate and cause multiple substitutions. A result of this is that in addition to the fact that the mechanisms of the substitution reactions are highly stereospecific, to yield virtually only the desired stereoisomer, the reaction conditions and product mixtures are such that epimerizations, which lead to undesired products, are generally avoided. In Finkelstein reactions, by contrast, epimerizations of starting materials and products can be a problem.

It is apparent that the 16-beta-triflate of estradiol,3,17-beta-diacetate (XIV) is a very useful intermediate for the introduction of halogens, especially iodine, stereospecifically, into the 16-position of estradiol. It is readily seen that the disclosed synthesis of this triflate as an intermediate or precursor for the syntheses of the desired products is very useful and important. It will be understood that when radioactive substituents of relatively short half-lives are used, the triflate intermediate may be prepared and sent to a location near a facility where the use of the radioactivity labeled estradiol is to take place. The halogen substitution reaction discussed above would then be performed at this location, the product purified, and the labeled estradiol would then be ready for use, before the radioisotope has had a chance to decay significantly.

It is foreseen that certain pharmaceutical compositions including a 16-$^{123}$I-17-beta-estradiol may be highly useful in imaging tissue with estrogen receptors located therein. Generally, for imaging compounds with a short half life and high specific activity, especially a specific activity greater than 5,000 curies per millimole, are preferred. For example, a mixture of ethanol and aqueous saline solution may be used. For imaging in humans, it is foreseen that a preferred injected concentration of the radioactive estradiol component in the dilutent is between 1.0 and 10.0 millicuries per millimeter, so that all of the radioactive compound may be injected in a relatively small volume.

A general synthesis of a triflate, XIV, was outlined in the reaction scheme illustrated above. The starting material, estrone (X) is readily available and upon treatment with isopropenyl acetate in acid readily forms an enol acetate XI.

The next step in the synthesis, that is, the oxidation with a peroxy acid to yield ketone XII, is both critical and somewhat unexpected. Upon treatment with meta-chloroperbenzoic acid, under base conditions, i.e. with sodium bicarbonate, enolate XI was observed to form ketone XII. This is in contrast to the chemical literature which suggests that oxidation of enolate XI with peroxy acids will form relatively stable epoxides. It will be understood that the isolation of ketone XII from the reaction with the peroxy acid facilitates a simple synthesis of the desired triflate XIV, since the oxidation yields only the 17-beta-acetate shown.

The next step in the synthesis, the reduction of the ketone XII to form alcohol XIII is performed with sodium borohydride (NaBH$_4$) and is observed to be rapid, of relatively high yield and highly stereospecific, giving reduction only from the alpha face to yield the 16-beta-hydroxy compound XIII. When lithium aluminum hydride (LiAlH$_4$) is used as the reducing agent, a mixture of alcohols is formed. It is believed that the reduction is controlled by steric factors and as long as reagent which is primarily sensitive to steric approach to reduction is utilized, the amount of alpha attack can be maximized and essentially only the 16-beta-hydroxy compound isolated.

The next step in the synthesis of the triflate XIV is formation thereof from the hydroxy compound XIII. This is readily achieved with triflic anhydride, (CF$_3$SO$_2$)$_2$ in the presence of pyridine. As reported above, the triflate XIV is relatively stable and can be easily purified by HPLC. THus, if any undesired side products are present from the previous reaction steps, they can be easily separated from the desired triflate product.

It is foreseen that the above synthesis is a generally useful, synthetic scheme for the generally stereospecific production of certain 16-halo-substituted-estradiols.

Beginning with estrone (XXX), the first part of the overall synthesis involves conversion to an enolate and protection of the 3-hydroxy group. In general:

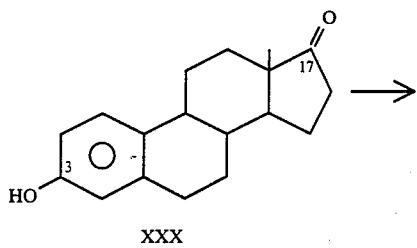

XXX

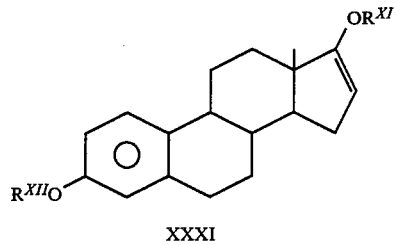

XXXI

In the specific example discussed earlier $R^{XI}$ and $R^{XII}$ were both acetyl groups. However, it is foreseen that other groups may be utilized and $R^{XI}$ and $R^{XII}$ need not be identical. For example, the 3-hydroxy group of estrone XXX might be protected by conversion to an ether or ester other than acetate before the 17-keto group is converted to an enolate. What is required, generally, is that $R^{XII}$ be a hydroxy-protecting group which can be readily hydrolyzed with acid for later removal and which is stable to the conditions of oxidation of the 17-enolate group. It is expected that certain silyl ethers, and esters other than acetates, may be used.

It is foreseen that under certain circumstances it may be desirable to leave the 3-hydroxy group unprotected, in which case $R^{XII}$ is H. It is foreseen that the presence of an -OH group at the 3-position will not significantly interfere with the later reactions, although it may be converted to an ester, for example a triflate, when the acid anhydride/pyridine or analogous reaction is run. This, however, is not foreseen to be a problem since whatever ester group is placed on the 3-position is likely to be easily removable during the final acid hydrolysis. Also, during the hydride reduction step, if the 3-hydroxy group is not protected, it may react with the hydride reagent, however, it is foreseen that this should not be a substantial problem if an excess of hydride reagent is used.

Protecting group $R^{XI}$, on the other hand, is an enolate protecting group of epoxide rearranging proclivity. Its general characteristics are that it can be used to trap an enol, as an enolate, and it can be removed by treatment with acid, once the enolate has been converted to a protected hydroxy group as in the next step. Also for the present purpose, group $R^{XI}$, should be able to function in the following oxidation and rearrangement:

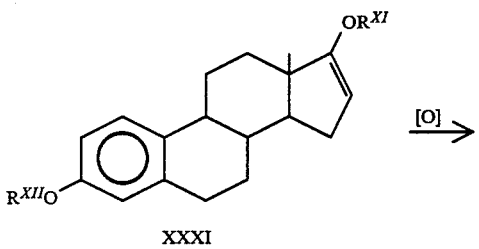

XXXI

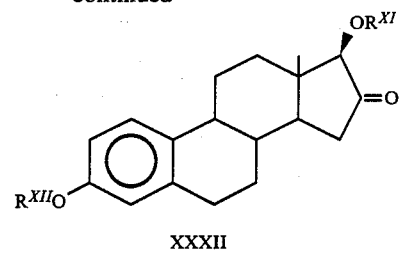

XXXII

The mechanism of the oxidation/rearrangement reaction is not fully understood, however it appears to yield, substantially stereospecifically, the 17-beat-16-keto compound XXXII. It is foreseen that enolate protecting groups other than —C(O)CH$_3$ may be utilized as $R^{XI}$.

The oxidation, [O], described above was conducted with meta-chloro perbenzoic acid (m-CPBA) as the oxidizing reagent. It is foreseen that other epoxide forming oxidizing reagents may be used, especially other peroxy acids. The conditions of the m-CPBA oxidations were generally basic with NaHCO$_3$, to protect the groups —OR$^{XI}$ and —OR$^{XII}$ from hydrolysis. Generally, neutral or basic conditions for the oxidation are preferred.

The next major step in the syntheses of 16-halo-substituted estradiols, according to the present invention, is the reduction, [R], of the 16-keto-3,17-beta-diprotected substrate (XXXIII), to the 16-beta-hydroxycompound (XXXIV):

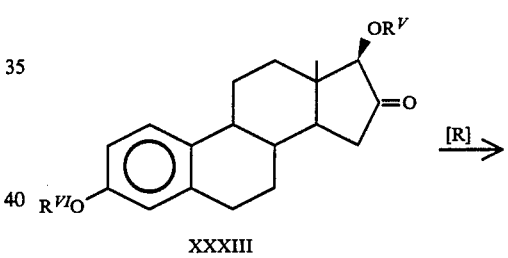

XXXIII

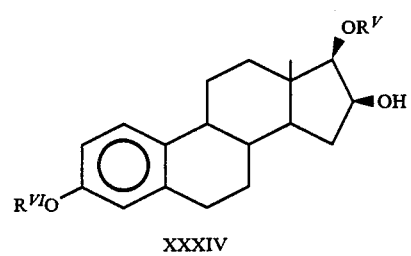

XXXIV

In most instances, the groups $R^V$ and $R^{VI}$ will be the same as $R^{XI}$ and $R^{XII}$ respectively. However, it is not necessary that they be so. It is foreseen that compound XXII could be converted to a compound XXXIII, having a different pair of protecting groups, through deprotection of the 3,17-beta-hydroxy groups and re-protection with protecting groups $R^{VI}$ and $R^V$. Such a conversion may be desirable to maximize certain aspects of either the preceding or following reactions, or to aid in the syntheses of derivatives with functional groups, not discussed herein, located at other positions in the substrate. It is foreseen that $R^{VI}$ may be almost any protecting group which can be readily removed by conventional acid hydrolysis techniques; and, $R^V$ is preferably a protecting group which, in addition, will not interfere with the direction of hydride attack during the reduction. Also, —OR$^V$ is preferably a relatively poor leaving group so it will not be displaced during reduction.

As mentioned above, the reduction [R] is accomplished with a hydride source or hydride reducing agent. Preferably, a hydride reagent is used which gives exclusive or generally exclusive alpha-attack to yield substantially only the 16-beta-hydroxy compound XXXIV upon aqueous workup. NaBH$_4$ has been found to work well, while LiAlH$_4$ gives a mixture. It is believed that reducing agents which are principally affected by steric factors will tend to maximize alpha-hydride attack.

The next general step in the reaction sequence is conversion of the 16-beta-hydroxy group into an appropriate leaving group for displacement by the halide ions:

bulky. Also, —OR, if compound XXVI is to be used for the halogen-displacement of —OR$^{II}$ at C-16, is preferably a poor enough leaving group so that substitution at C-17 will not compete with substitution at C-16 in the next step. It is believed that if —OR is a carboxy group, this latter requirement will generally be fulfilled.

On the other hand, —OR$^{II}$ is preferably an excellent leaving group in substitution reactions. The currently preferred group is a triflate group, —OSO$_2$CF$_3$, formed from reaction of the 16-alcohol, XXXV, with triflic-anhydride and a base, preferably pyridine. Generally, a weak base at low nucleophilicity is preferred so that completing substitution and elimination reactions are minimized. In general, —OR$^{II}$ will usually be an ester leaving group, generally an ester of a sulfonic acid. It is preferred that the group —OR$^{II}$ not be too readily hydrolyzable or deprotection may occur before desired.

If the 16-alpha-halo compound is desired, the next step in the synthesis is as follows:

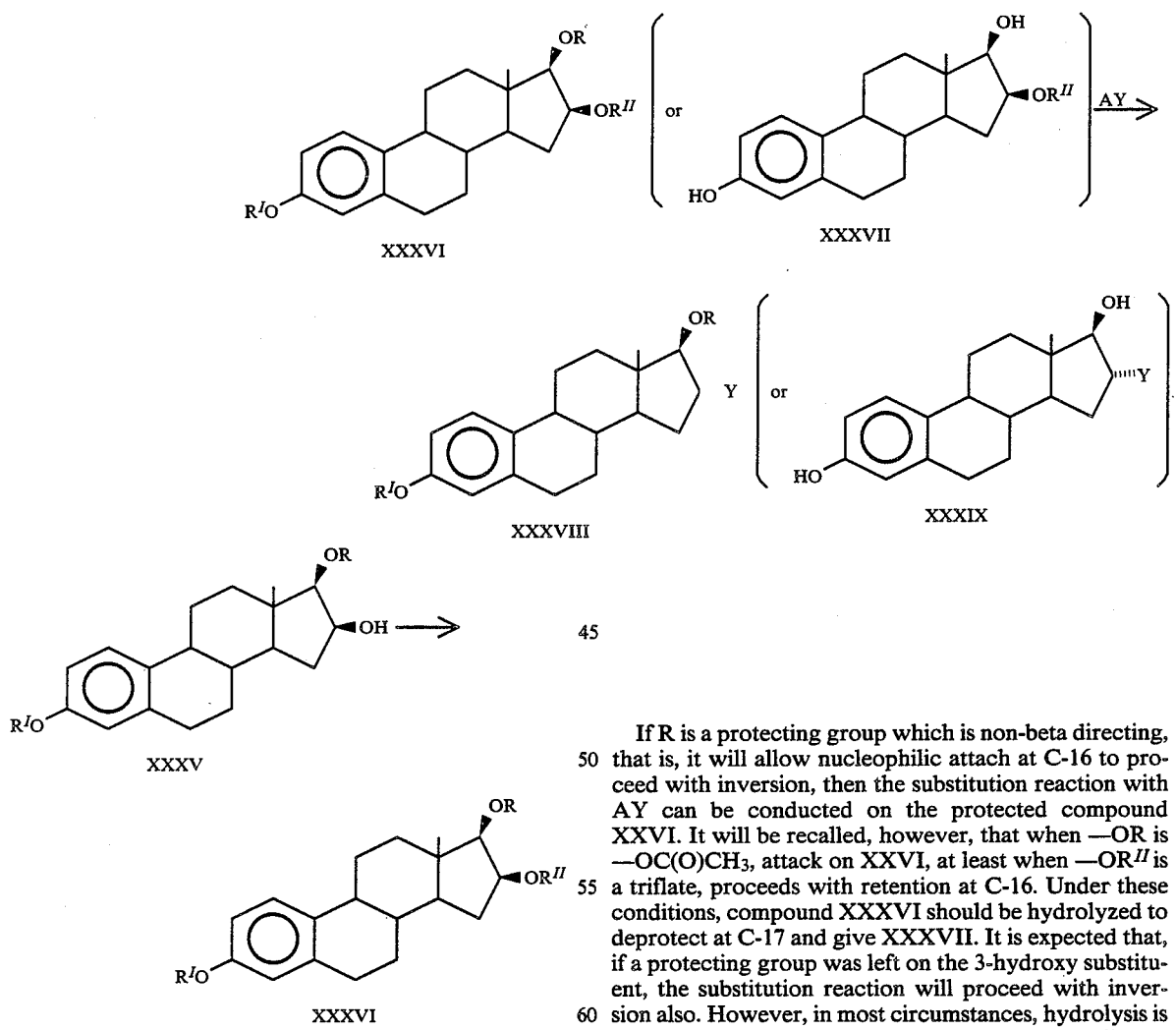

It will be understood that R and R$^I$, in XXXV, need not be identical to R$^V$ and R$^{VI}$, respectively, in XXXIV, although generally they will be. R$^I$ is preferably a protecting group which is readily hydrolyzed with acid. R is preferably a readily hydrolyzable protecting group which does not interfere with the formation of —OR$^{II}$. Generally this requires —OR to be relatively non- If R is a protecting group which is non-beta directing, that is, it will allow nucleophilic attach at C-16 to proceed with inversion, then the substitution reaction with AY can be conducted on the protected compound XXVI. It will be recalled, however, that when —OR is —OC(O)CH$_3$, attack on XXVI, at least when —OR$^{II}$ is a triflate, proceeds with retention at C-16. Under these conditions, compound XXXVI should be hydrolyzed to deprotect at C-17 and give XXXVII. It is expected that, if a protecting group was left on the 3-hydroxy substituent, the substitution reaction will proceed with inversion also. However, in most circumstances, hydrolysis is C-17 will be sufficient to deprotect at C-3 as well.

It will be understood that differing combinations of —OR and —OR$^{II}$ will yield attack with inversion. If —OR is —OAc and —OR$^{II}$ is triflate, then attack with AY, where AY is NH$_4$I or NaI, proceeds with inversion at C-16.

If the 16-beta-halo-substituted compound is desired, the reaction will be as follows:

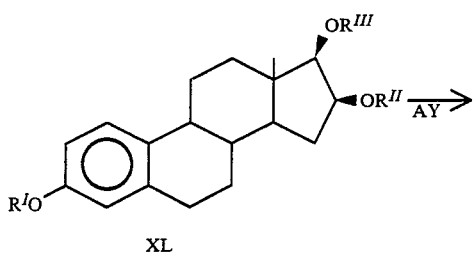

XL

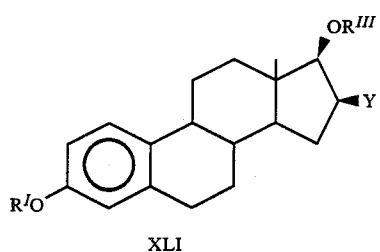

XLI

In XL, —OR$^{III}$ is a protected hydroxy with beta-directing capabilities, when associated with —OR$^{II}$. Such a combination, as stated above, is when —OR$^{III}$ is -OAc and —OR$^{II}$ is —OSO$_2$CF$_3$. It is foreseen that other combinations with similar chemical features may also be used. The group —OR$^{III}$ may be a group —OR$^{II}$ from the previously discussed series.

It will be understood that hydrolyses of the protected C-3 and C-17 groups may be conducted, whenever appropriate, for the desired diols to be formed. These will be generally acid hydrolyses so that the halo-substituent at C-16 will be undisturbed.

The following examples illustrate the high efficiency and versatility of the present invention in application to form certain 16-substituted estradiols. In addition, the following examples are for purposes of illustration of the invention and should not be interpreted as limiting the scope of applicants' invention.

EXPERIMENT 1

Synthesis of the 16-beta-triflate of Estradiol, 3,17-beta-diacetate (XIV)

A. Formation of the Enol Acetate (XI).

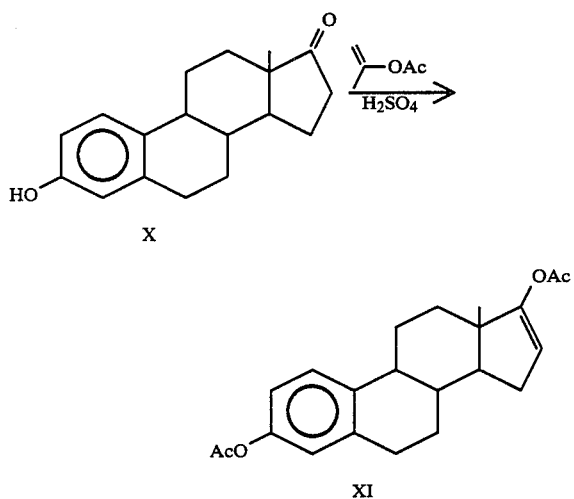

A solution of 10.0 grams (g.) (37.0 millimoles) of estrone (x) was dissolved in 70 milliliters (ml.) of isopropenyl acetate and 10 ml. of catalyst solution. The catalyst solution comprised 0.2 ml. of concentrated H$_2$SO$_4$ dissolved in 10 ml. of isopropenyl acetate. The reaction mixture was heated to boiling and approximately 10 ml of distillate was taken off over a period of 0.5 hours. An additional 30 ml. of isopropenyl acetate was added along with approximately 1 ml of catalyst solution and boiling was continued until approximately 50 ml. of distillate was taken off. At this time another 30 ml. of isopropenyl acetate and 1 ml. of catalyst solution was added and boiling continued until a second 30 ml. of distillate was taken off.

The reaction mixture was cooled to room temperature and dilluted with 200 ml. of ether. The ether solution was washed with cold concentrated sodium bicarbonate solution The solution was then washed with water, dried and the solvent was evaporated. The residue was taken up in 50 ml. of acetone and passed through a silica gel column (500 grams in a 5 cm. by 30 cm. column) developed with hexane acetone 4/1. Upon removal from the column, the solid was recrystallized from ethanol (120 ml.). The product was a yellow solid (9,88 grams, 75% yield, melting point 145 to 148 degrees centigrade). An NMR spectrum was run of the resulting product and it was consistent with the structure for the desired product (XI).

B. Oxidation of the Enolate (XI) to Form 16-keto-estradiol, 3,17-beta-diacetate (XII).

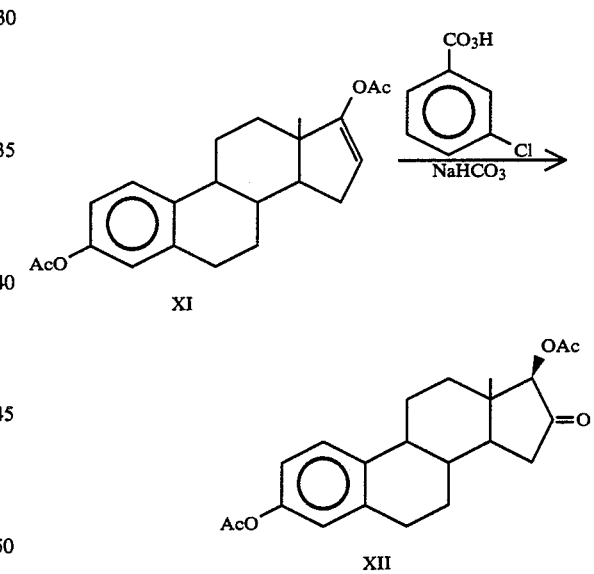

A 0.5 millimolar aqueous sodium bicarbonate solution was prepared and 100 ml. of the solution was added to 150 ml. of chloroform in a 500 ml. round bottom flask. The diacetate (XII) (9.88 grams, 27.9 millimoles) was added to the chloroform solution in one portion. After the steroid had dissolved, 6.90 grams (40.0 millimoles) of m-chloroperoxyperbenzoic acid was added in one portion and the reaction mixture was stirred for 15 hours at room temperature. The aqueous phase was then removed in a separatory funnel and the organic phase was washed with two 50 ml. portions of 10% sodium bisulfate solution and then two 50 ml. portions of saturated aqueous sodium bicarbonate solution. The organic solution was dried over sodium sulfate, filtered, and evaporated to dryness to give a yellow semisolid which was recrystallized from enthanol to give a white solid (5.50 grams, 53% yield, melting point 146 to 149 degrees centigrade.) This solid was recrystallized again from ethanol to give a white solid (3.54 grams, 34% yield, melting point 151 to 153 degrees centigrade, [alpha]$_D$=54.5 (EtOH), one spot by TLC (hexane: acetone, 4/1, silica gel) (NMR analysis confirmed that only isomer XII was formed.)

C. Reduction of Ketone XII to Form 16-beta-hydroxy-17-beta-estradiol, 3,17-beta-diacetate XIII.

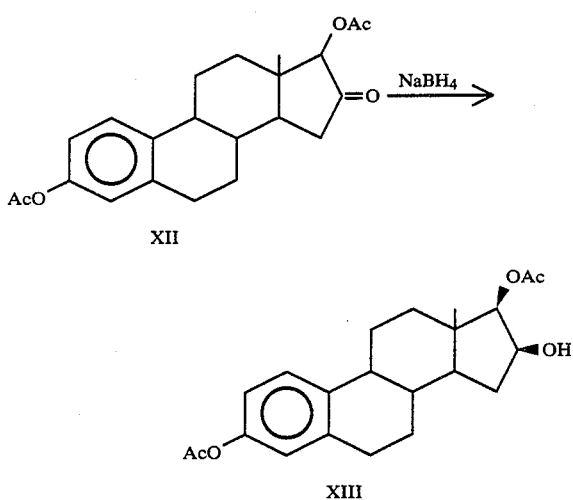

The 16-oxo-estradiaol-3,17-diacetate (XII) (1.04 grams, 2.81 millimoles) was dissolved in 80 ml. of isopropanol and 35 milligrams (0.92 millimoles) of sodium borohydride was added in one portion at room temperature. After 0.5 hours the reaction mixture was treated with 3 drops of concentrated hydrochloric acid and evaporated to dryness. The residue was purified by preparative TLC (hexane:acetone, 3:1, silica gel, eight 1,000 microplates) with the highest R$_f$ component eluted and isolated as a white solid (144 milligrams, 14% yield, melting point 75 to 80 degrees centigrade; NMR in CDCl$_3$, consistent with the above stated structure XIII).

D. Formation of Triflate XIV from Diacetate XIII.

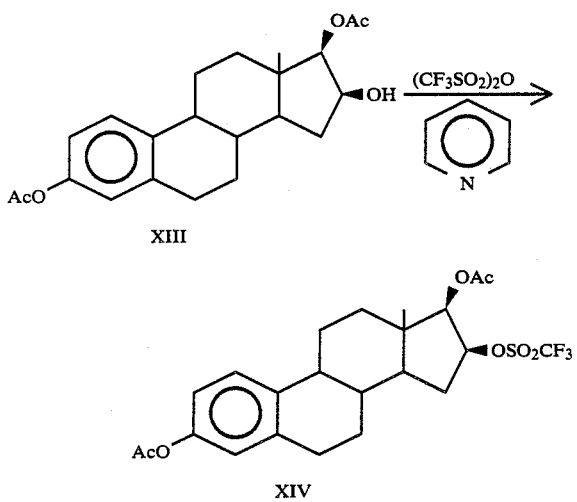

Fifty-four milligrams (0.145 millimoles) of the 16-beta-17-beta-estriol-3,17-diacetate (XIII) was dissolved in 0.5 ml. of deutero-chloroform in a septum top vial and 21 microliters (21 milligrams, 0.260 millimoles) of pyridine was added. The vial was cooled in an ice bath and 40 microliters (65 milligrams, 0.237 millimoles) of triflic anhydride was added via syringe. After one hour the reaction mixture was filtered and the filtrate purified by preparative TLC (hexane:acetone, 3:1 silica gel, one 1,000 microplate) to give a colorless solid (59 milligrams, 81% yield, melting point 50 to 58 degrees; NMR in CDCl$_3$, consistent with the above stated structure XIV).

The deprotected diol is readily isolated from the diacetate by hydrolysis with concentrated HCl in tert-butanol (t-BuOH) analogously to the hydrolysis conducted in experiment 3 below.

EXPERIMENT 2

Preparation of 16-alpha-$^{123}$I-17-beta-estradiol

The radioisotope I-123 is generally available as either NH$_4$$^{123}$I or Na$^{123}$I. In the experiments described below, NH$_4$$^{123}$I was utilized as the source of the iodine isotope, however analogous experiments have been run with Na$^{123}$I, which was found to function satisfactorily for the present purpose. The experimental procedure for either is substantially identical.

The NH$_4$$^{123}$I was received from Atomic Energy of Canada, Ltd (AECL) in a solution of one percent amonium hydroxide. The volume of the solution was between 0.5 and 1.0 milliliter (ml). The container was a sealed 10 ml. vial with a rubber septum.

The vial was placed in a lead container and equipped with a gas and vacuum line via a 19 guage needle. A 25-guage needle was inserted through the septum so that an air flow through the vial could be maintained. The apparatus was heated, at 80 degrees centigrade, until dryness was obtained in the vial.

An acidic solution of t-butanol was prepared by adding 1 ml. of concentrated H$_2$SO$_4$ to 99 ml. of t-butanol. A sufficient amount of the one percent H$_2$SO$_4$ solution was added to the NH$_4$$^{123}$I vial to neutralize the sodium hydroxide. This generally required the same volume of acid solution (0.5 to 1.0 ml.) as the amount of base solution that was originally present in the vial. Testing paper was utilized to test the pH and the acid solution was added until the pH paper showed the pH range to be between 6.5 and 7.5 or about neutral.

After the above, the amount of radioactivity contained in the solution was generally between 8 and 10 millicurries (mCi). Approximately one-half of the solution (4 to 5 mCi) was transferred to a 0.30 ml. micro vial fitted with a cap.

200 micrograms of 16-beta-triflate-17-beta-estradiol was dissolved in 200 microliters of t-Butanol and transferred to the reaction vial already containing the NH$_4$$^{123}$I. One crystal of 18-crown-6 ether (500 to 1,000 micrograms) was added to the reaction solution.

By evaporation with an air stream passing through the vial, the reaction mixture was concentrated to a volume of approximately 100 microliters. At this point, the vial was sealed and heated to boiling for 90 minutes. After heating, the vial was cooled and the contents transferred to a micro-injection vial and injected into an HPLC. The HPLC conditions utilized are described below.

After the product was collected from the HPLC the solvent was evaporated by an air stream and the residue dissolved in a 5 percent absolute ethanol/saline solution. The solutions was filtered through a 0.22 micron filter for sterilization.

The HPLC conditions were as follows:

1. A Waters model 720 instrument was used in association with a WISP 710B automatic injector.
2. The detector was a model 440 UV/Vis absorbence detector with the UV detector wave length being at 254 or 280 nanometers, as selected.
3. The column was a C18 RP 10 micron, 8 millimeter internal diameter, radial packed column, available from Waters.
4. The solvent system utilized was a 50/50 acetonitrile/water mixture with the flow rate set at 1.0 ml. per minute.

Under the above conditions, the reaction products came off the column after approximately 19 minutes.

When the substitution was conducted, as described above, for between 1 and 1.5 hours, the yield of substituted product was about 40-50% (based on measurements with non-radioactive NH$_4$I). When the heating for substitution was allowed to continue for an extra 2-3 hours, yields were increased to about 70% (again based on experiments with nonradioactive materials).

Although for some imagery, limits of detection require an estimated specific activity of 30,000 Ci/mmole, it is expected that the product, immediately off the column, had a specific activity of near maximum, 237,000 Ci/mmole.

EXPERIMENT 3

Preparation of 16-beta-$^{123}$I-17-beta-estradiol

Commercially available I-123 in the form of NH$_4$$^{123}$I, in one percent sodium hydroxide solution, was neutralized with acid and prepared for reaction with a substrate, in a manner as described above for preparation of the 16-alpha isomer. The neutralized NH$_4$$^{123}$I solution was diluted with 500 microliters of t-butanol and approximately one-half of the solution (4 to 5 milliCuries) was transferred to a micro reaction vial.

Two hundred micrograms of estradiol, 16-beta-triflate,3,17-beta-diacetate was dissolved in 200 microliters of t-butanol and transferred to the micro reaction vial. One crystal of 18-crown-6 ether (500 to 1,000 micrograms) was added to the reaction solution. The reaction mixture was concentrated, by drying with an air stream, to a volume of approximately 100 microliters, and was heated to boiling for approximately 90 minutes.

After substitution, 100 microliters of concentrated HCl was added to the solution and heating was continued for about 60 minutes. After the hydrolysis, the reaction vial was cooled to room temperature and the contents of the vial were injected to the HPLC system described above and the desired product collected from the column.

Yields of the 16-beta-isomer appeared comparable to the 16-alpha-isomer described in Experiment 2 above. The specific activity of the product was also comparable.

It is to be understood that while certain forms of the present invention have been illustrated and described herein, it is not to be limited to the specific processes, forms, or compositions described.

What is claimed and desired to be secured by Letters Patent is as follows:

1. A compound for use as an imaging agent; said compound being 16-alpha-$^{123}$I-17-beta-estradiol having a specific activity of greater than 2,000 Ci/mmole.
2. The compound according to claim 1 wherein said specific activity is at least 5,000 Ci/mmole.
3. The composition comprising the compound according to claim 1 and a pharmaceutically acceptable diluent.
4. A pharmaceutical compound for use as an imaging agent; said compound being 16-$^{123}$I-17-beta-estradiol having a specific activity of greater than 2,000 Ci/mmole.
5. The compound according to claim 4 wherein:
   (a) said estradiol is 16-alpha-$^{123}$I-17-beta-estradiol; and
   (b) said specific activity is at least 5,000 Ci/mmole.
6. The compound according to claim 4 wherein:
   (a) said estradiol is 16-beta-$^{123}$I-17-beta-estradiol.
7. The composition comprising the compound according to claim 4 and a pharmaceutically acceptable diluent.
8. The composition according to claim 7 wherein said diluent is a mixture of saline solution and ethanol.

* * * * *